(12) United States Patent
Gostein et al.

(10) Patent No.: US 7,365,864 B2
(45) Date of Patent: Apr. 29, 2008

(54) METHOD OF DETERMINING PROPERTIES OF PATTERNED THIN FILM METAL STRUCTURES USING TRANSIENT THERMAL RESPONSE

(75) Inventors: Michael Gostein, Quincy, MA (US); Alexei Maznev, Natick, MA (US)

(73) Assignee: Advanced Metrology Systems LLC, Natick, MA (US)

( * ) Notice: Subject to any disclaimer, the term of this patent is extended or adjusted under 35 U.S.C. 154(b) by 282 days.

(21) Appl. No.: 10/547,637

(22) PCT Filed: Dec. 10, 2003

(86) PCT No.: PCT/IB03/05876

§ 371 (c)(1),
(2), (4) Date: Aug. 30, 2005

(87) PCT Pub. No.: WO2004/055476

PCT Pub. Date: Jul. 1, 2004

(65) Prior Publication Data

US 2006/0203876 A1 Sep. 14, 2006

Related U.S. Application Data

(60) Provisional application No. 60/433,312, filed on Dec. 13, 2002.

(51) Int. Cl.
*G01B 11/14* (2006.01)

(52) U.S. Cl. .................. 356/625; 356/432; 374/45; 73/800

(58) Field of Classification Search .............. 356/432, 356/625; 374/45; 73/800
See application file for complete search history.

(56) References Cited

U.S. PATENT DOCUMENTS

| 6,256,100 B1 * | 7/2001 | Banet et al. ............. 356/432 |
| 6,587,794 B1 * | 7/2003 | Maznev .................... 702/28 |
| 2002/0030826 A1 * | 3/2002 | Chalmers et al. ........ 356/630 |

FOREIGN PATENT DOCUMENTS

EP 1 150 173 A2 10/2001

* cited by examiner

*Primary Examiner*—Layla G. Lauchman
*Assistant Examiner*—Iyabo S Alli
(74) *Attorney, Agent, or Firm*—Goodwin Procter LLP

(57) ABSTRACT

The present invention measures a structure including multiple narrow metallic regions, each being disposed between neighboring regions comprising a second, non-metallic material. One step of the method is exciting the structure by irradiating it with a spatially periodic excitation field made up of excitation stripes in order to generate a thermal grating. Other steps are diffracting a probe laser beam off the thermal grating to form a signal beam; detecting the signal beam as a function of time to generate a signal waveform; and determining at least one property of the structure based on a thermal component of the signal waveform.

30 Claims, 7 Drawing Sheets

METHOD OF DETERMINING PROPERTIES OF PATTERNED THIN FILM METAL STRUCTURES USING TRANSIENT THERMAL RESPONSE

This application claims priority to and benefit of International (PCT) Patent Application No. PCT/IB03/05876, which claims priority to and benefit of U.S. provisional application Ser. No. 60/433,312 filed Dec. 13, 2002, which are incorporated herein by reference.

The invention relates to the field of optical metrology to determine properties of a sample, e.g., a thin film structure.

Fabrication of microelectronic devices typically includes metal structures that are formed by a multi-step thin film deposition and patterning process. For example, in one process, a metal such as copper is deposited onto a wafer having a dielectric layer that has been patterned by etching to have a series of cutouts or trenches. Next, the wafer is planarized, for example, by chemical-mechanical planarization (CMP) to remove excess metal above the original dielectric film surface. The resulting structure is a series of separated narrow metallic regions embedded in dielectric. These regions are usually elliptical or rectangular, but can take any shape. Narrow is herein defined as having a width of less than 5 microns. Examples of such patterns include arrays of embedded parallel metal lines and two-dimensional arrays of embedded metal posts.

Non-contact optical methods of measuring such structures are in great demand for industrial process monitoring and control. Parameters of most interest for process control applications include dimensions of the metal regions in the structures. It is also important to detect the presence of metal residue on top of the structure that may remain at the end of a polishing step, compromising its electrical properties. However, optical measurement of metal structures is a challenging problem because metal films are typically opaque.

In one known method, described in the prior art U.S. Pat. No. 6,256,100, herein incorporated by reference, a metal array structure on an integrated circuit is probed using an impulsive stimulated thermal scattering (ISTS) surface acoustic wave spectrometer. As shown in FIG. 1, in this technique, the sample structure 1 is excited with a short pulse of laser light imaged to form a grating pattern 2 on the sample surface by the interference of two beams 3,3'. Absorption of light under each of the bright stripes 5 of the grating pattern 2 causes local heating of the sample, which results in sudden periodic expansion launching acoustic waves at the sample surface. The acoustic wave propagation can be seen in enlarged portion 8. As this surface acoustic wave (SAW) propagates in the plane of the film, it also modulates the diffracted signal beam 6' intensity, resulting in an oscillatory component (henceforth "acoustic component") in the detected signal.

The above-described technique has been employed to measure the thickness of film layers by analysis of the SAW frequency spectrum. This technique is henceforth referred to as "frequency analysis." U.S. Pat. No. 6,256,100 referenced above describes an application of frequency analysis to measure the effective thickness of composite layers formed of narrow (i.e. micron or submicron width) metal structures embedded in an insulating dielectric material.

A limitation of this method is that it measures a single parameter, the SAW frequency, which is sensitive to both the thickness and lateral dimensions of the metal regions in the structure. In addition, this method does not distinguish between the presence of metal residue and the variation of the thickness or lateral dimensions of the structure. It is therefore desirable to use additional information contained in the ISTS signal in order to overcome these limitations.

In fact, it is known in the prior art (see Rogers et al, Appl. Phys. A 58, 523-534 (1994)) that the ISTS signal contains a contribution due to the spatially periodic displacement and reflectivity variation associated with the temperature profile, referred to as a thermal grating. This contribution gives rise to a component of the signal (henceforth "thermal component") that varies more slowly than that due to the acoustic oscillations. However, the thermal component has not been used in the prior art to measure patterned metal structures.

Accordingly, it would be desirable to provide a method that takes advantage of additional properties of the detected signal.

The present invention meets the need for a method that takes advantage of additional properties of the detected signal in one aspect. The method measures a structure including multiple narrow metallic regions, each being disposed between neighboring regions comprising a second, non-metallic material. One step of the method is exciting the structure by irradiating it with a spatially periodic excitation field made up of excitation stripes in order to generate a thermal grating. Other steps are diffracting a probe laser beam off the thermal grating to form a signal beam; detecting the signal beam as a function of time to generate a signal waveform; and determining at least one property of the structure based on a thermal component of the signal waveform.

In one embodiment, the spatially periodic excitation field made up of excitation stripes has a period ranging from 1 to 20 microns. In another embodiment, the narrow metallic regions each have a width of less than 5 microns. In another embodiment, the narrow metallic regions each have a width of less than 1 micron.

In one embodiment, the structure includes an array of metal lines. In another embodiment, the spatially periodic excitation field is arranged such that the excitation stripes are parallel to the metal lines.

In yet another embodiment, the structure includes a two-dimensional array of metal posts.

In another embodiment, the at least one property includes a width of at least one of the narrow metallic regions. In another embodiment, the at least one property includes a thickness of at least one of the narrow metallic regions. In another embodiment, the at least one property includes a thickness of or presence of metal residue.

In one embodiment, the determining step includes determining at least one property of the structure based on a decay rate of the signal waveform.

In another embodiment, the exciting and detecting steps are repeated at multiple periods of the excitation field and the multiple resulting waveforms are analyzed to determine the at least one property of the structure. In another embodiment, the multiple waveforms are analyzed to determine at least two properties of the structure.

In still another embodiment, the determining step includes analysis of the signal waveform with an empirical calibration. In another embodiment, the determining step includes analysis of the signal waveform with a theoretical model based on selected thermal and elastic properties of the structure.

In one aspect, a method for measuring a structure comprising multiple narrow metallic regions, each being disposed between neighboring regions comprising a second, non-metallic material, includes several steps. One step is exciting the structure by irradiating it with a spatially periodic excitation field made up of excitation stripes in order to generate a thermal grating and acoustic waves. Other steps are diffracting a probe laser beam off the thermal grating and acoustic waves to form a signal beam; detecting the signal beam as a function of time to generate a signal waveform; and determining at least one property of the structure based on both a thermal component and an acoustic component of the signal waveform.

In one embodiment, the spatially periodic excitation field made up of excitation stripes has a period ranging from 1 to 20 microns. In another embodiment, the narrow metallic regions each have a width of less than 5 microns.

In one embodiment, the structure includes an array of metal lines. In another embodiment, the spatially periodic excitation field is arranged such that the excitation stripes are parallel to the metal lines. In another embodiment, the structure includes a two-dimensional array of metal posts.

In still another embodiment, the at least one property is a width of at least one of the narrow metallic region. In another embodiment, the at least one property is a thickness of at least one of the narrow metallic regions. In another embodiment, the at least one property is a thickness or presence of metal residue.

In one embodiment, the exciting and detecting steps are repeated at multiple periods of the excitation pattern and the-multiple signal waveforms are analyzed to determine at least one property of the structure.

In another embodiment, the signal waveform is analyzed to determine at least two properties of the structure.

In another embodiment, the determining step includes analysis of the signal waveform with an empirical calibration. In another embodiment, the determining step includes analysis of the signal waveform with a theoretical model based on selected thermal and elastic properties of the structure. In another embodiment, the determining step includes determining both thickness and width of at least one of the narrow metallic regions of the structure.

In another embodiment, the determining step includes determining both thickness or presence of metal residue and at least one dimension of the array structure. The invention provides many advantages that are evident from the following description, drawings, and claims.

The invention may be more completely understood in reference to the following figures.

n the newly invented method, the thermal component of the signal waveform is used to analyze properties of the structure. This technique is herein referred to as "thermal analysis."

Figure 2:
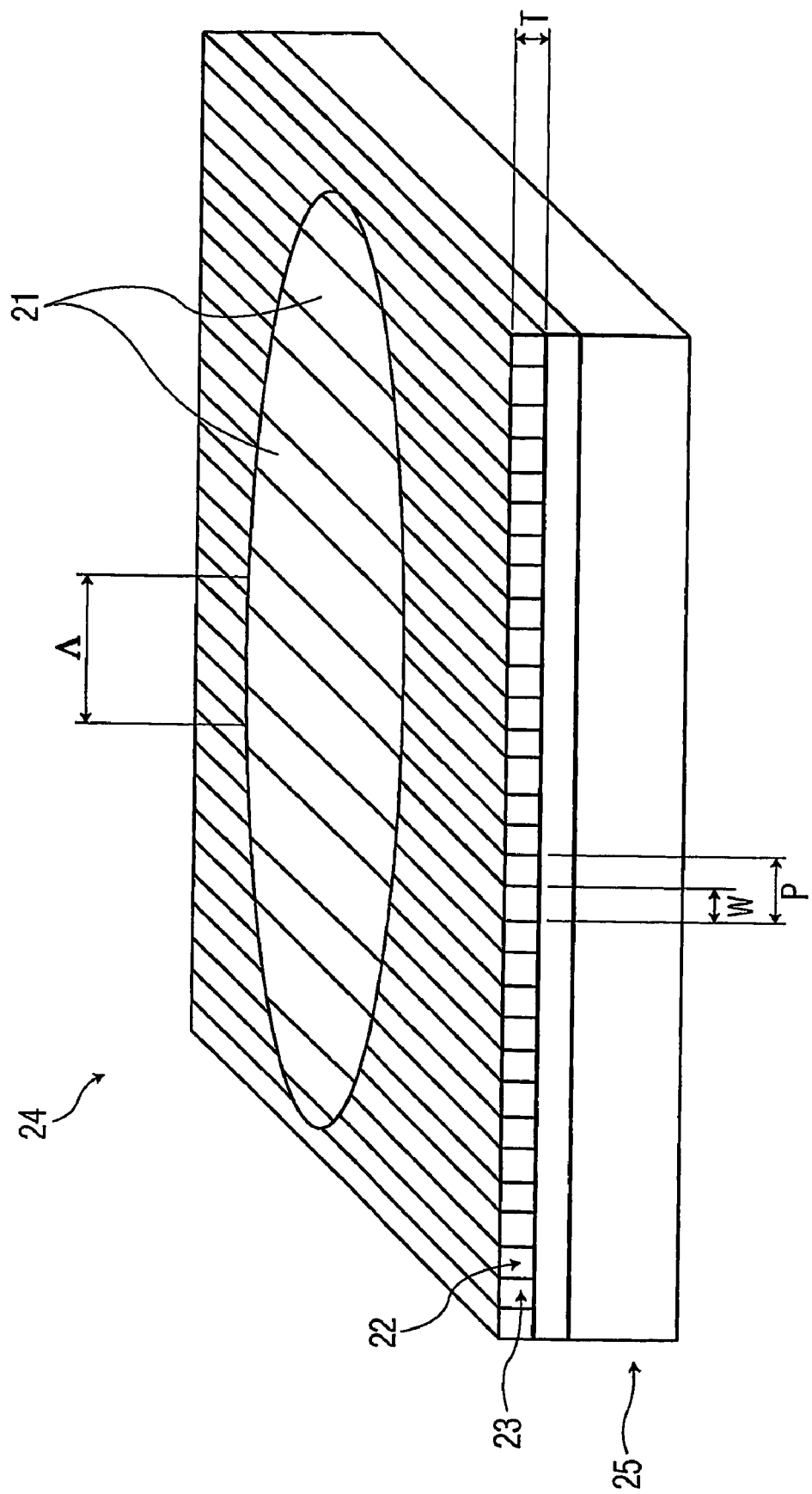
FIG. 2 depicts measurement of line array structures with ISTS.
Figure 3:
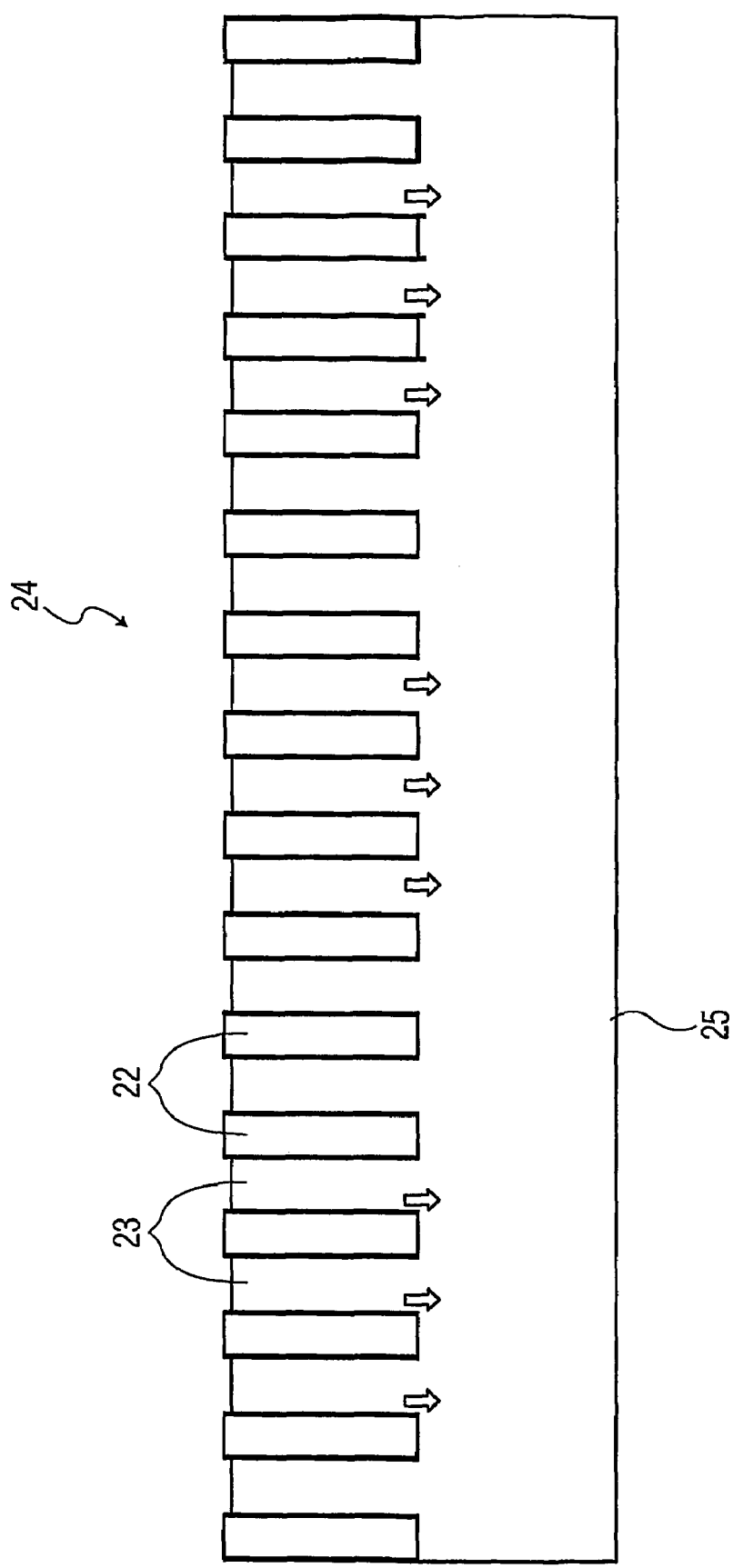
FIG. 3 depicts heat dissipation of a thermal grating.

FIG. 2 illustrates application of the invented method to the case of an array structure comprising multiple parallel metal lines of width W and Thickness T. In this case the excitation stripes 21 should be arranged parallel to the lines 22, 23 of the array structure 24, as shown in FIG. 2. If the excitation period Λ is large compared to the array pitch P, then with the excitation stripes 21 oriented parallel to the lines 22, 23 of the array structure 24, dissipation of the thermal grating occurs as individual metal lines 22 cool by heat transfer to the surrounding dielectric material 23 and eventually to the substrate 25, as illustrated in FIG. 3. The rate of heat flow between the excitation stripes 21 is relatively low, because of the poor thermal conduction of the dielectric 23. Therefore the characteristic thermal decay time is much longer than would be observed with the excitation stripes 21 oriented perpendicular to the metal lines 22 (in which case the thermal grating would decay by heat transfer along the thermally conductive metal).

Figure 4:
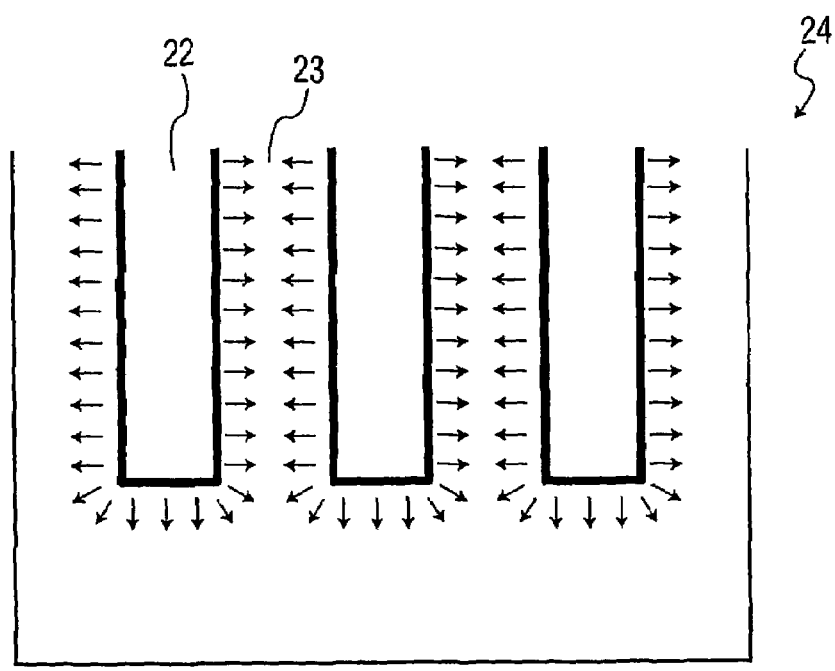
FIG. 4 depicts heat flow from individual metal lines to their immediately surrounding dielectric material.

Initially the heat flow is primarily from individual metal lines 22 to their immediately surrounding dielectric material 23, as shown in FIG. 4. Therefore, at early times after the initial excitation the decay rate R of the thermal grating is approximately proportional to the ratio of the surface area per unit length to the volume per unit length of the metal lines 22, i.e.

$$R \propto \frac{2T+W}{WT} = \frac{2}{W} + \frac{1}{T}$$

Therefore, the decay rate depends on the thickness and width of the metal lines 22 in the array structure 24.

Figure 5:
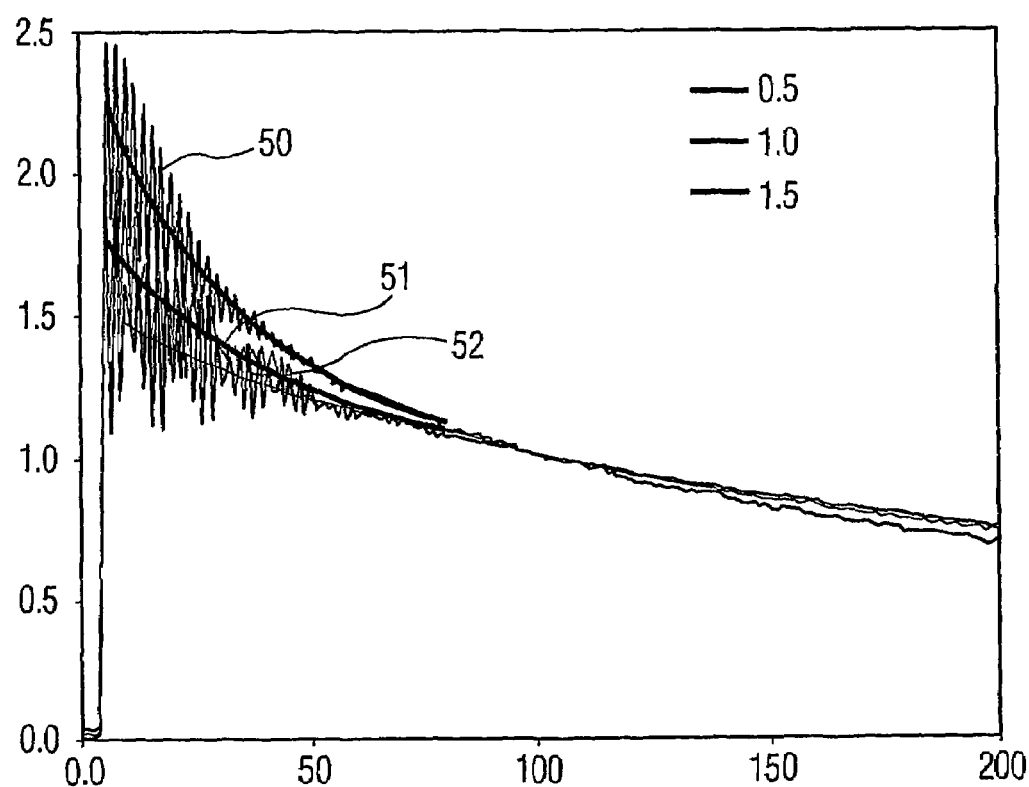
FIG. 5 depicts signal waveforms.
Figure 6:
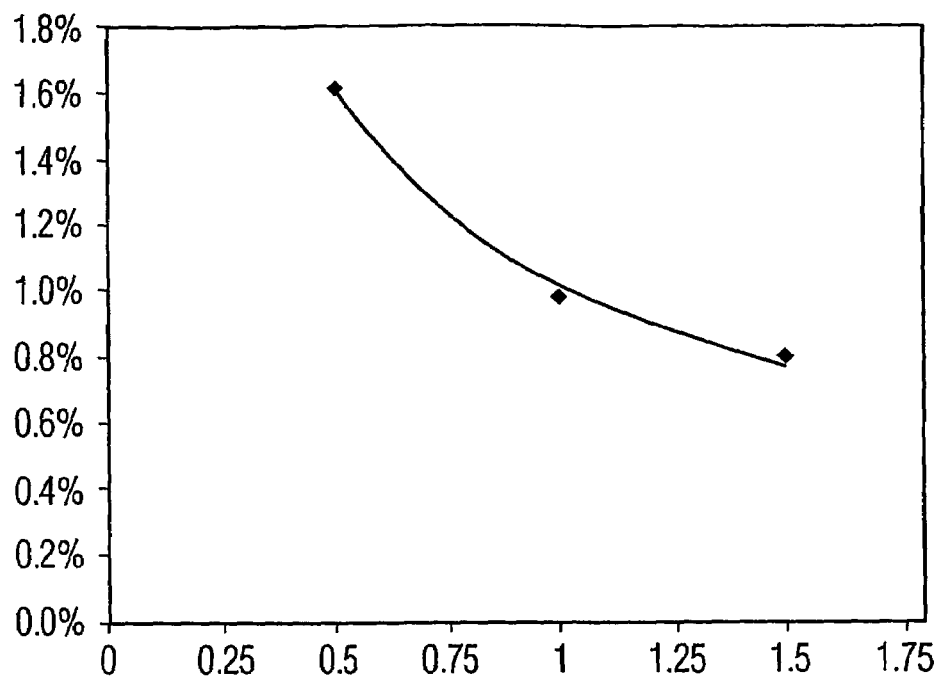
FIG. 6 depicts the correlation between linewidth and decay rate.

This dependence is illustrated by the representative signal waveforms 50, 51, 52 in FIG. 5. These waveforms 50, 51, 52 were acquired from structures of copper lines embedded in silicon dioxide dielectric. The vertical axis represents normalized signal and the horizontal axis represents time in nanoseconds. The line array structures used to generate waveforms 50, 51, 52 all had a pitch of 2 microns, with copper linewidths of 0.5, 1.0, and 1.5 microns, respectively, and thickness approximately 0.5 microns. Signals were acquired with excitation period of Λ=8.3 microns to maintain the requirement Λ>>P mentioned above, and the excitation stripes were oriented parallel to the metal lines. In FIG. 5 the waveforms have been normalized to have equal intensity at a time of 100 ns. As expected from Equation (1), the initial decay rate of the thermal grating increases as the linewidth is reduced. To measure the thermal component decay rate of the waveforms 50, 51, 52, each waveform was fitted to a smooth polynomial curve in the time interval before 100 ns, and the slope of the fitted curve initially after the excitation was calculated. This slope is defined as the decay rate. FIG. 6 plots the decay rate (on the vertical axis in percent of signal change per nanosecond) determined from these fits versus the copper linewidth (on the horizontal axis in microns). FIG. 6 confirms the expected correlation between linewidth and decay rate. Note that at times after ~100 ns, the decay rates of all three structures are approximately equal, because in this time region the heat diffusion length is large compared to the array dimensions. The characteristic diffusion length is proportional the square root of time t, and the surface temperature should therefore vary approximately as $\sqrt{t}$ for all three curves in the late-time region.

Figure 7:
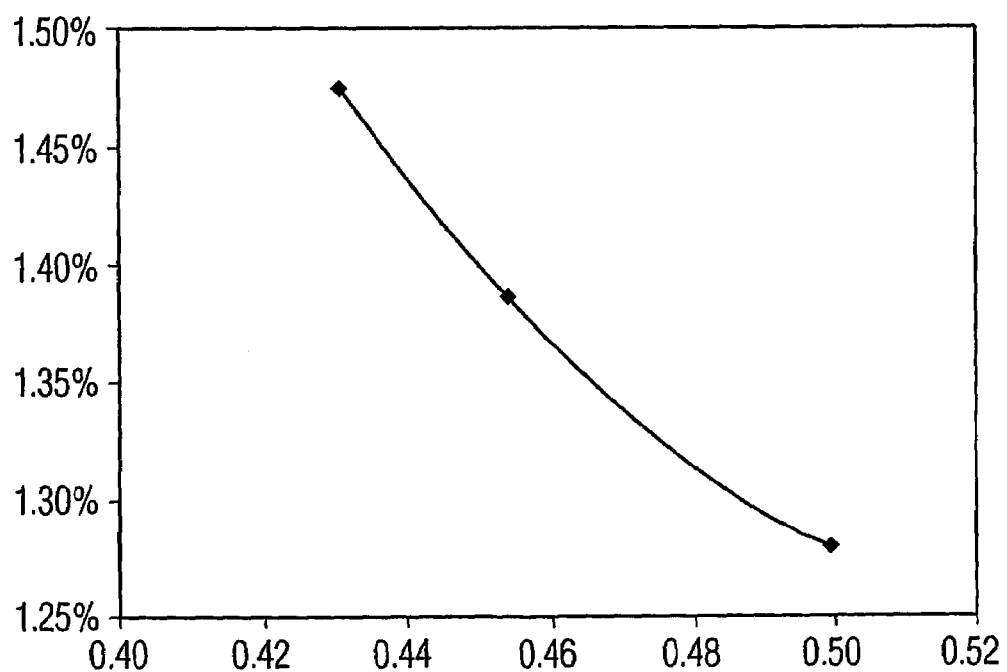
FIG. 7 depicts the decay rate sensitivity to the thickness T of the array structure.

Note from Eq. (1) that it is expected that the decay rate is sensitive to the thickness T of the array structure 24. This dependence is illustrated in FIG. 7, which shows the decay rate (on the vertical axis in percent of signal change per nanosecond) measured on several structures of equal linewidth W=0.25 microns, but varying thickness T (on the horizontal axis in microns). All three structures had array pitch 0.5 microns. Again, the figure illustrates the expected correlation between decay rate and thickness.

Note also that the relative sensitivity of the decay rate to either thickness or linewidth depends on the aspect ratio $$\alpha \equiv \frac{T}{W}$$

Subsituting α into Eq. (1), obtains $$R \propto \frac{(2\alpha+1)}{\alpha}\frac{1}{W}$$

Therefore, in the limit α>>1, R is proportional to 1/W and is roughly independent of T. This fact means that, for high-aspect-ratio structures where the width W and thickness T are known approximately but both may vary due to process variations, the thermal analysis method described herein can determine width W nearly independently of the thickness T.

The limit of large aspect ratio corresponds to a case of practical importance in the manufacture of integrated circuits, where the cutting-edge of integrated circuit technology involves definition of ever-narrower lines on the circuitry. Today's leading-edge technologies may have metal lines with a width as narrow as 0.1 microns, with typical thickness of 0.5 microns, i.e. an aspect ratio of ~5. Aspect ratios are expected to increase with each successive IC technology generation. Furthermore, for any IC fabrication process, there is typically considerable process-related variation in the minimum linewidth. Therefore, the ability to measure this parameter accurately is important.

Taking advantage of Eq. (3) for high aspect ratio structures, the "thermal analysis" method can be combined with the "frequency analysis" method described earlier to determine, in the former case, the linewidth W, and, in the latter case, the cross-sectional area W×T. This therefore permits determination of both W and T independently, which could not be achieved with the frequency analysis method alone. Combination of the two methods therefore represents one advantageous embodiment of the invention.

Note that Eqs. (1) and (3) are simplified approximations, and a more elaborate physical analysis of the decay profiles will yield more accurate results. This more detailed analysis takes into account the thermal properties (i.e. heat capacity, thermal conductivity, density, thermal expansion coefficient, etc.) of the materials and involves the solution of a set of differential equations describing the heat flow and the temperature distribution. It also determines the effect of the temperature distribution on the surface corrugation and the resulting effect on the diffracted probe beam intensity versus time. This more detailed analysis can be included as part of a computer software program to analyze the measurement results in an automated way.

Compared to the existing "frequency analysis" method, the invented "thermal analysis" method achieves several advancements that extend the capability of ISTS-based instruments for application to array structures.

One such advantage is that the invention provides the capability to determine the widths of metal lines in line arrays. For high-aspect-ratio structures, this width can be determined with only nominal information about the array thickness.

Another advantage is a method to determine the thickness of array structures that may be superior to frequency-based analysis of SAWs in specific circumstances. These circumstances could include the following: a) cases where the underlying film stack information is not sufficiently well specified to use the frequency-based analysis; b) cases involving array structures built upon specific underlying film stacks that result in poor sensitivity for frequency-based measurement; c) cases involving structures where the array pitch is approximately equal to the minimum SAW wavelength of the measuring instrument; and d) cases involving array structures that consist of a grid or mesh pattern.

Also, by combining the use of the invented method relying upon thermal measurement along with the existing frequency-based method, it will be possible to determine both the thickness and the width of lines in array structures, as described above. The invention provides many additional advantages that are evident from the description, drawings, and claims.

Metal Residue Detection

In another application, the invented method is used to measure metal residue on top of an array structure.

Figure 1:
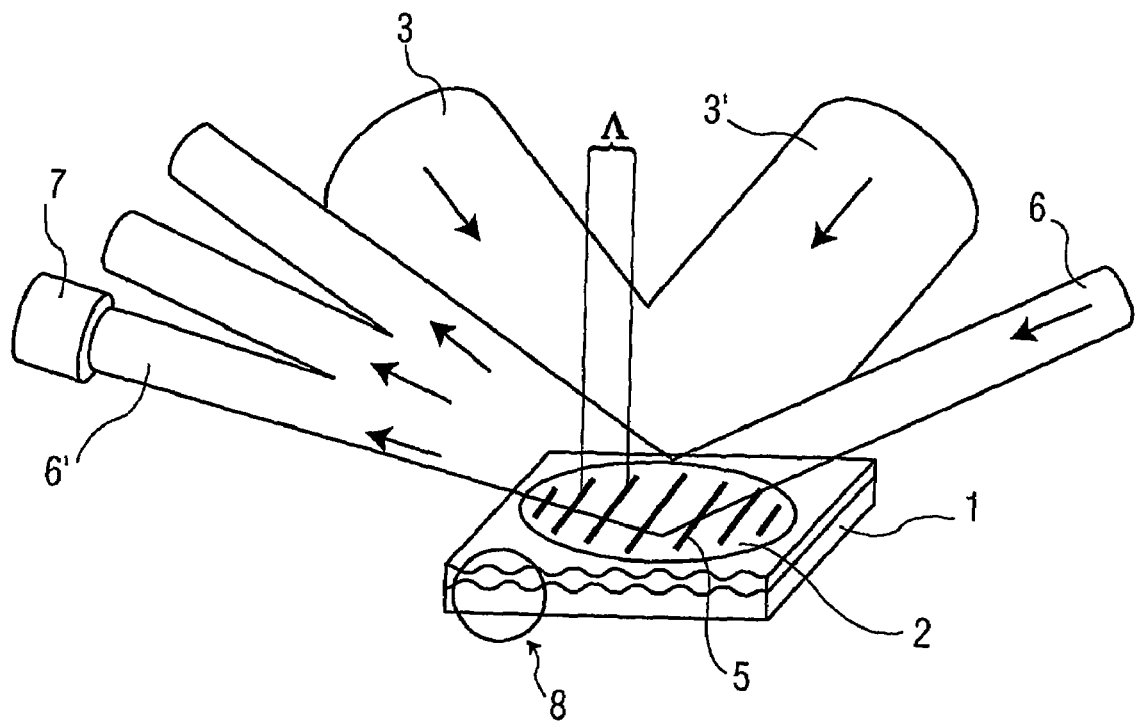
FIG. 1 depicts a metal thin film structure on an integrated circuit probed using impulsive stimulated thermal scattering according to a prior art method.
Figure 1A:
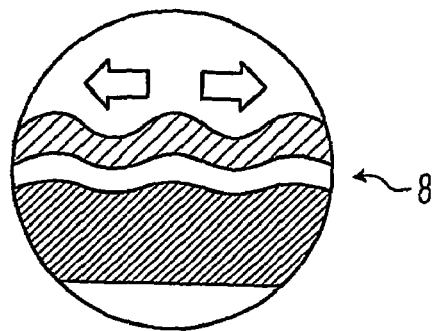
Figure 8:
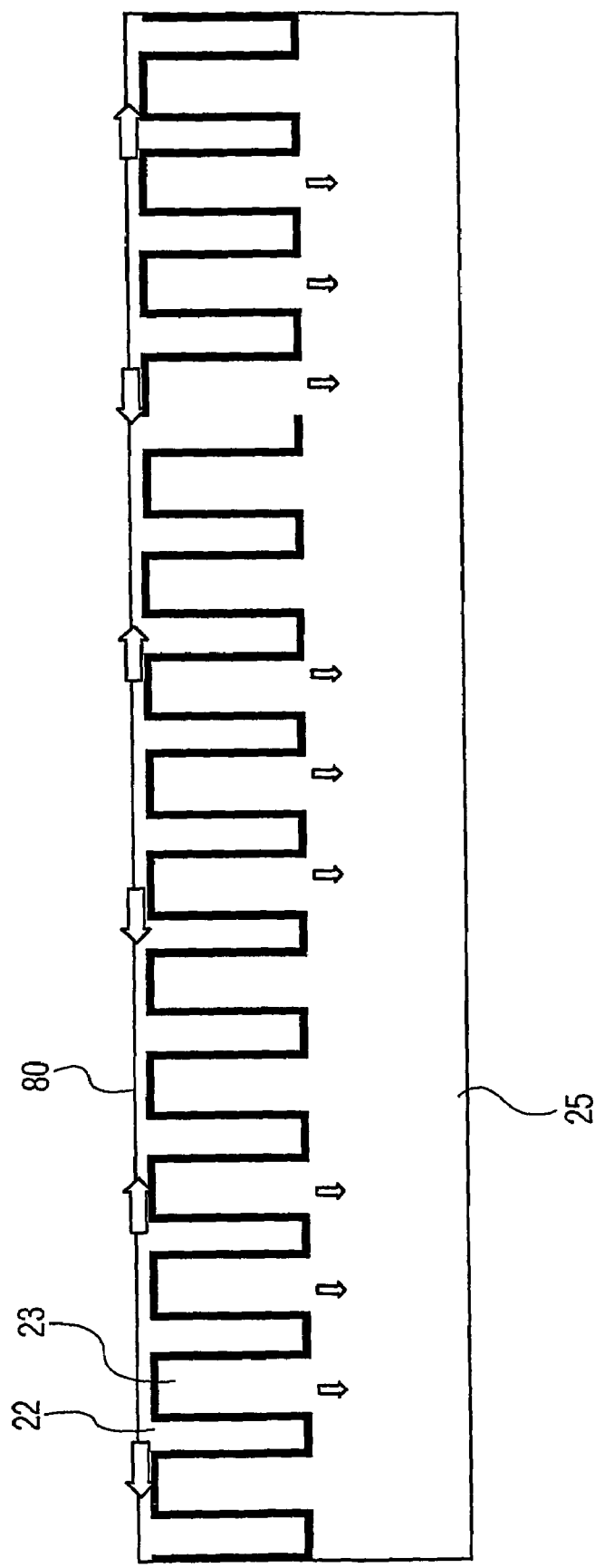
FIG. 8 depicts heat flow in the presence of a metal residue on top of the array.

For example, in the case of a line array, the line array structure 24 is illuminated with the grating excitation pattern 2 oriented parallel to the lines 22, 23 in the array structure 24. (See FIGS. 1 and 2) In this orientation, and in the absence of metal residue (FIG. 4), dissipation of the thermal grating occurs as individual metal lines 22 cool by heat transfer to the surrounding dielectric material 23 and eventually to the substrate 25. The rate of heat flow is relatively low, because of the poor conduction of the dielectric 23. FIG. 8 depicts the presence of a metal residue 80 on top of the line array 24. Metal residue 80 will greatly increase the heat conduction rate from one metal line 22 to its neighbor. In this case, the signal decay rate will be much higher, because as the temperature becomes laterally uniform the thermal corrugation diminishes and the diffracted beam intensity decreases.

The decay rate of the signal therefore can be correlated to the presence of a metal residue 80 on top of the measured line array structure 24. By measuring the characteristic decay rate of a line array structure 24 and analyzing with a theoretical or empirical model, the metal residue 80 thickness can be measured.

Figure 9:
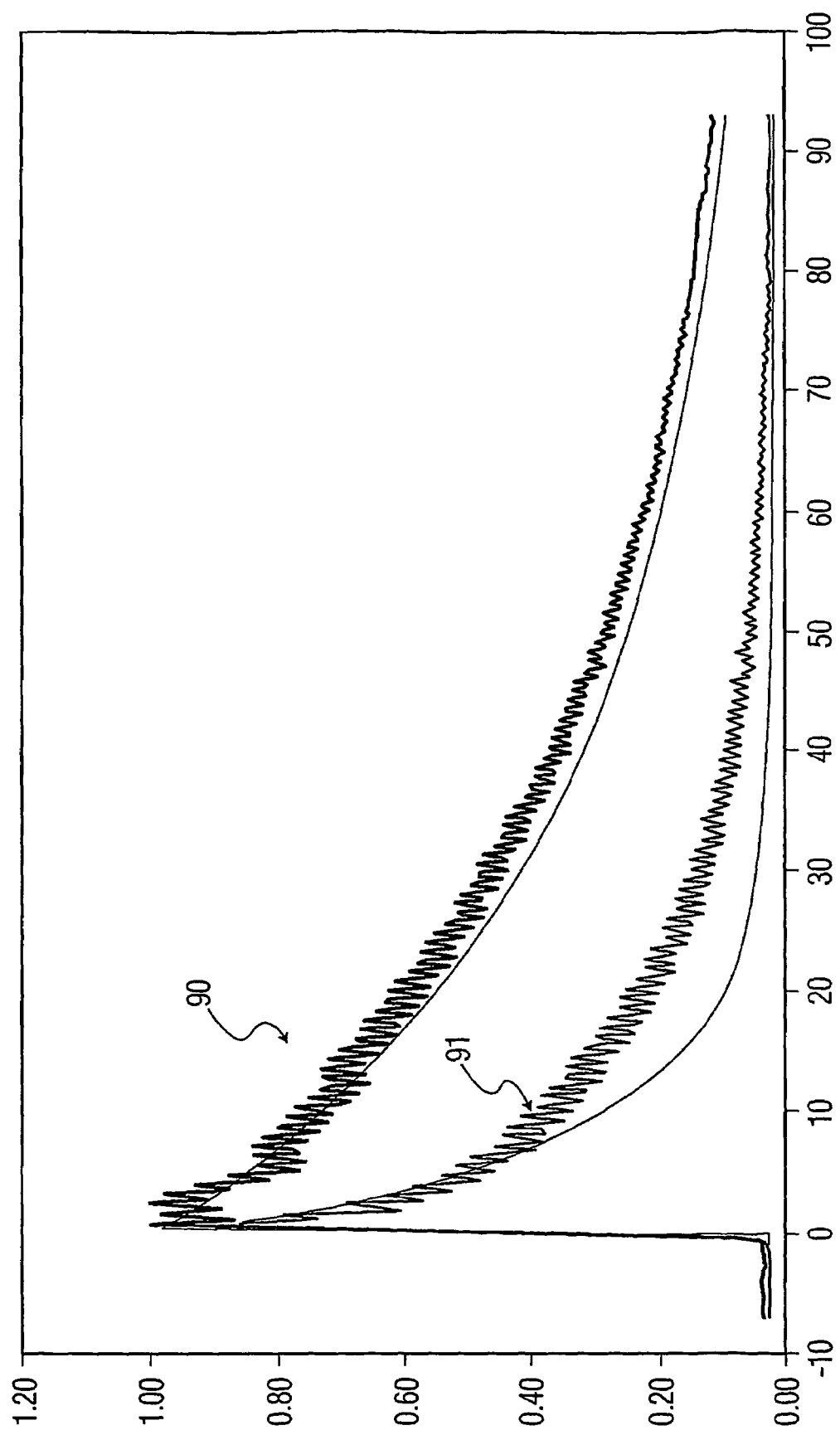
FIG. 9 depicts signal waveforms generated with a metal residue and without a metal residue atop the line array.

The two waveforms 90 and 91 in FIG. 9 show an example of the capability for residue detection. The waveforms were each acquired on different parts of a test sample after polishing, with one waveform measured in a region that was completely cleared of metal (e.g., corresponding to signal waveform 90), and the other measured in an underpolished region with an estimated 200 Å of remaining copper residue (e.g., corresponding to signal waveform 91). The line array structures 24 measured were arrays of 0.35 micron wide copper lines with 0.35 micron silicon dioxide spaces, and the structures were measured using a 2 micron thermal grating period. The residue-covered structure clearly shows a much faster decay of the thermal grating during the time immediately following the excitation laser pulse (e.g., signal waveform 91). Fitting the initial portion of each waveform to an exponential curve (with fits shown in the figure) yields characteristic decay rates of 0.03 ns$^{-1}$ and 0.128 ns$^{-1}$ for the copper-cleared and residue-covered portions of the sample, respectively.

The method could also be applied to other array structures, e.g. a two-dimensional array of metal posts.

One advantageous embodiment of the invention is to measure the decay rate of the sample structure using multiple values of the thermal grating period, Λ, and to analyze the group of values using a theoretical or empirical model. This improves the accuracy of the measurement by allowing discrimination between the effects of metal residue and those of other sample variations that could also affect the decay rate. Using multiple grating periods allows this discrimination because different types of sample variation result in different trends of decay rate versus Λ.

Another advantageous embodiment of the invention is to combine the measurement and analysis of the thermal component with a measurement and analysis of the acoustic component of the signal. This yields additional information about the sample and improves the accuracy of the residue measurement because the thermal and acoustic signal components respond differently to variations of different parameters.

The invention provides many additional advantages that are evident from the description, drawings, and claims.

The preceding expressions and examples are exemplary and are not intended to limit the scope of the claims that follow.

The invention claimed is:

1. A method for measuring a structure comprising multiple narrow metallic regions, each being disposed between neighboring regions comprising a second, non-metallic material, comprising:
    exciting the structure by irradiating it with a spatially periodic excitation field made up of excitation stripes in order to generate a thermal grating;
    diffracting a probe laser beam off the thermal grating to form a signal beam;
    detecting the signal beam as a function of time to generate a signal waveform; and
    determining at least one property of the structure based on a thermal component of the signal waveform.

2. The method of claim 1, wherein the spatially periodic excitation field made up of excitation stripes has a period ranging from 1 to 20 microns.

3. The method of claim 1, wherein the narrow metallic regions each have a width of less than 5 microns.

4. The method of claim 1, wherein the narrow metallic regions each have a width of less than 1 micron.

5. The method of claim 1, wherein the structure comprises an array of metal lines.

6. The method of claim 5, wherein the spatially periodic excitation field is arranged such that the excitation stripes are parallel to the metal lines.

7. The method of claim 1, wherein the structure comprises a two-dimensional array of metal regions.

8. The method of claim 1, wherein the at least one property comprises a width of at least one of the narrow metallic regions.

9. The method of claim 1, wherein the at least one property comprises a thickness of at least one of the narrow metallic regions.

10. The method of claim 1, wherein the at least one property comprises a thickness of or presence of metal residue.

11. The method of claim 1, wherein the determining step further comprises determining at least one property of the structure based on a decay rate of the signal waveform.

12. The method of claim 1, wherein the exciting and detecting steps are repeated at multiple periods of the excitation field and the multiple resulting waveforms are analyzed to determine the at least one property of the structure.

13. The method of claim 12, wherein the multiple waveforms are analyzed to determine at least two properties of the structure.

14. The method of claim 1, wherein the determining step comprises analysis of the signal waveform with an empirical calibration.

15. The method of claim 1, wherein the determining step comprises analysis of the signal waveform with a theoretical model based on selected thermal and elastic properties of the structure.

16. A method for measuring a structure comprising multiple narrow metallic regions, each being disposed between neighboring regions comprising a second, non-metallic material, comprising:
    exciting the structure by irradiating it with a spatially periodic excitation field made up of excitation stripes in order to generate a thermal grating and acoustic waves;
    diffracting a probe laser beam off the thermal grating and acoustic waves to form a signal beam;
    detecting the signal beam as a function of time to generate a signal waveform; and
    determining at least one property of the structure based on both a thermal component and an acoustic component of the signal waveform.

17. The method of claim 16, wherein the spatially periodic excitation field made up of excitation stripes has a period ranging from 1 to 20 microns.

18. The method of claim 16, wherein the narrow metallic regions each have a width of less than 5 microns.

19. The method of claim 16, wherein the structure comprises an array of metal lines.

20. The method of claim 19, wherein the spatially periodic excitation field is arranged such that the excitation stripes are parallel to the metal lines.

21. The method of claim 16, wherein the structure comprises a two-dimensional array of metal regions.

22. The method of claim 16, wherein the at least one property comprises a width of at least one of the narrow metallic regions.

23. The method of claim 16, wherein the at least one property comprises a thickness of at least one of the narrow metallic regions.

24. The method of claim 16, wherein the at least one property comprises a thickness or presence of metal residue.

25. The method of claim 16, wherein the exciting and detecting steps are repeated at multiple periods of the excitation pattern and the multiple signal waveforms are analyzed to determine at least one property of the structure.

26. The method of claim 16, wherein the signal waveform is analyzed to determine at least two properties of the structure.

27. The method of claim 16, wherein the determining step comprises analysis of the signal waveform with an empirical calibration.

28. The method of claim 16, wherein the determining step comprises analysis of the signal waveform with a theoretical model based on selected thermal and elastic properties of the structure.

29. The method of claim 16, wherein the determining step further comprises determining both thickness and width of at least one of the narrow metallic regions of the structure.

30. The method of claim 16, wherein the determining step further comprises determining both thickness or presence of metal residue and at least one dimension of the array structure.

* * * * *